(12) United States Patent
Deslauriers et al.

(10) Patent No.: US 6,520,281 B1
(45) Date of Patent: Feb. 18, 2003

(54) ELASTOMERIC ANTI-MICROBIAL STETHOSCOPE DIAPHRAGM

(75) Inventors: Richard J. Deslauriers, Waterbury, CT (US); Robert T. Potash, South Windsor, CT (US); Lewis W. Chappel, New Hartford, CT (US)

(73) Assignee: Doctors Research Group, Plymouth, CT (US)

( * ) Notice: Subject to any disclaimer, the term of this patent is extended or adjusted under 35 U.S.C. 154(b) by 0 days.

(21) Appl. No.: 09/640,917

(22) Filed: Aug. 18, 2000

(51) Int. Cl.[7] .................................. A61B 7/02
(52) U.S. Cl. ........................ 181/131; 600/528
(58) Field of Search ...................... 181/131, 129, 181/130; 381/67; 600/528; D24/134

(56) References Cited

U.S. PATENT DOCUMENTS

| | | | | |
|---|---|---|---|---|
| 4,461,368 A | * | 7/1984 | Plourde | 181/131 |
| 5,365,023 A | * | 11/1994 | Lawton | 181/131 |
| 5,428,193 A | * | 6/1995 | Mandiberg | 181/131 |
| 5,686,706 A | * | 11/1997 | Wurzburger | 181/131 |
| 5,747,751 A | * | 5/1998 | Weckerle et al. | 181/131 |
| 5,921,941 A | * | 7/1999 | Longobardo et al. | 600/528 |
| 5,949,032 A | * | 9/1999 | Wurzburger | 181/131 |
| 6,019,186 A | * | 2/2000 | Zambrano | 181/131 |
| 6,019,187 A | * | 2/2000 | Appavu | 181/131 |

* cited by examiner

Primary Examiner—Robert E. Nappi
Assistant Examiner—Edgardo San Martin

(57) ABSTRACT

A replaceable and disposable elastomeric soft diaphragm or cover for use with a stethoscope whereby said elastomeric soft diaphragm or cover is a molded piece of elastomer being sufficiently flexible allowing for simple application and removal, whereby said diaphragm or cover, when attached, forms an airtight seal with the stethoscope, and whereby device may act as a soft diaphragm in stethoscopes with removable rigid diaphragms with said rigid diaphragm removed or as a cover where said rigid diaphragm remains attached to said stethoscope.

14 Claims, 3 Drawing Sheets

FIGURE #1
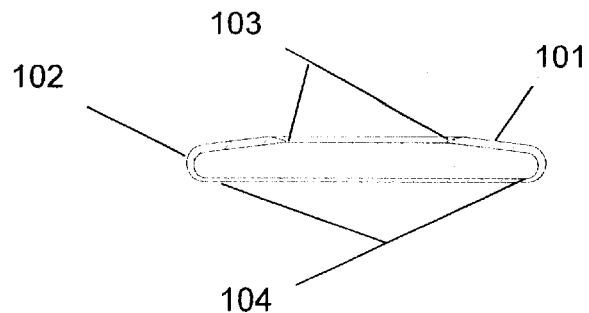
FIGURE #2
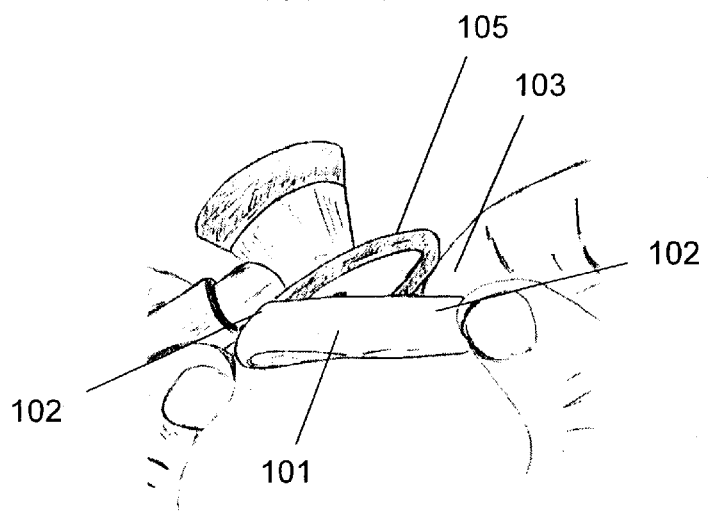
FIGURE #3
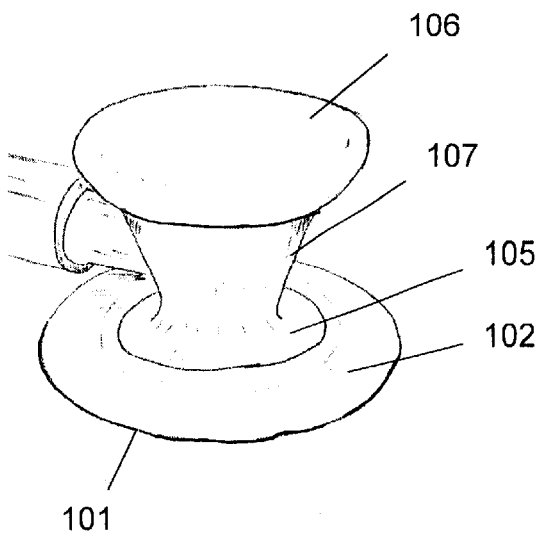

FIGURE #4
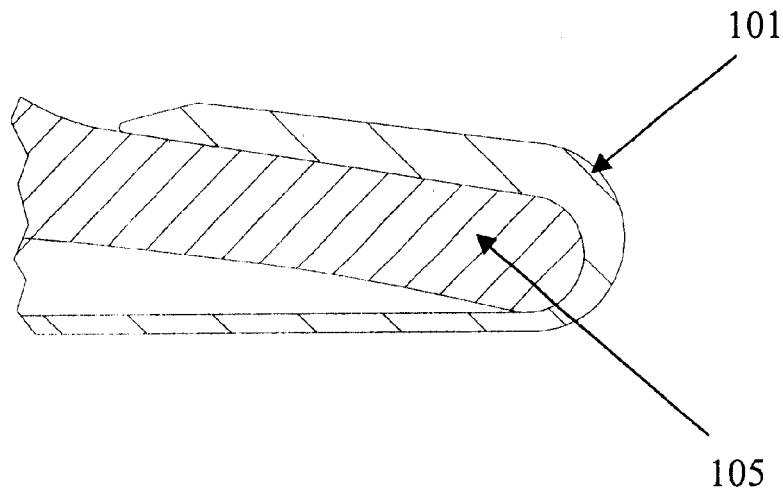
FIGURE #5
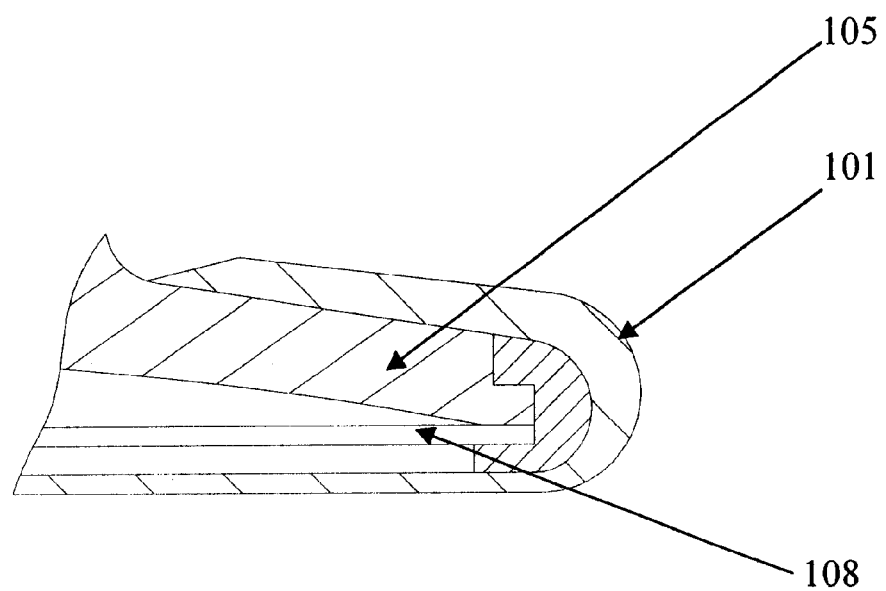

FIGURE #6
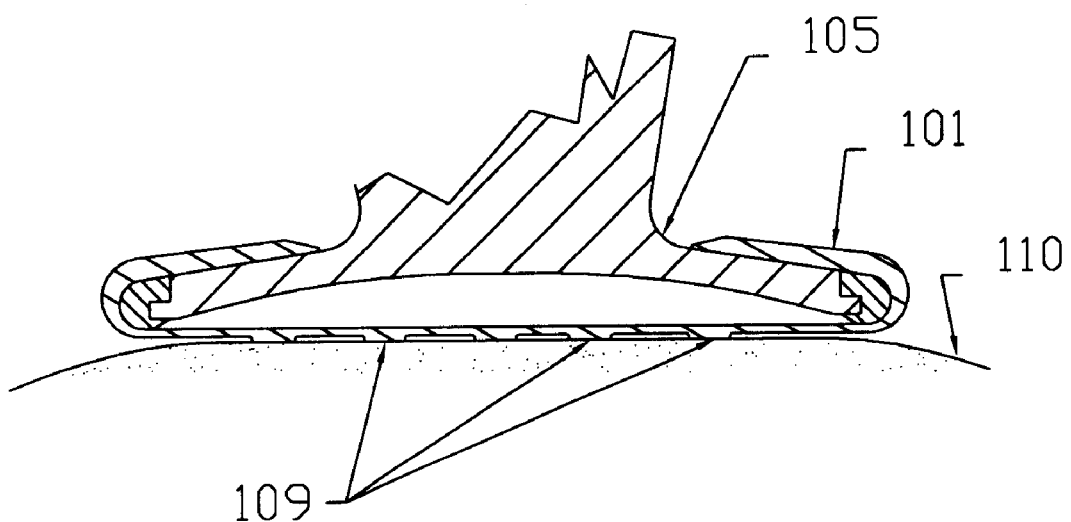

ELASTOMERIC ANTI-MICROBIAL STETHOSCOPE DIAPHRAGM

CROSS-REFERENCE TO RELATED APPLICATIONS:

Not Applicable

STATEMENT REGARDING FEDERALLY SPONSORED RESEARCH OR DEVELOPMENT:

Not Applicable

BACKGROUND OF THE INVENTION

1. Field of the Invention

This invention relates to the field of medical devices and medical device accessories preventing the transmission of bacteria from one patient to another. The stethoscope is a medical instrument that aids the doctor in listening to a patient's internal body sounds, such as the heartbeat, by placing the head of the stethoscope onto a patient's skin. However, the head of the stethoscope may attract harmful bacteria and pathogens when it comes in contact with the skin of a patient, and these harmful agents may subsequently be spread to a second patient when the same stethoscope is applied to the second patient's skin.

A common problem for many hospitals and health care facilities is the transmission of infections between patients that results from using shared medical devices, and the difficulty that is associated with keeping those medical devices sterile. Traditional measures being employed focus on the use disposable medical supplies or those medical supplies that may be sterilized after they have come in contact with a patient. Furthermore, training is provided on the proper precautions to take when dealing with multiple patients with the intent of eliminating the spread of inter-patient infections.

One medical device that is particularly susceptible of carrying diseases from patient to patient is the stethoscope. This invention relates to a disposable elastic diaphragm to be used in conjunction with or as a replacement to the rigid diaphragm coming standard on stethoscopes and which does not require the use of any adhesives or other dispensing units for application to the stethoscope. Said invention can be further enhanced through the use of a sterile material and impregnating the said material with anti-microbial agents the disposable diaphragm offers increased protection against the transmission of harmful contaminants that may come in contact with the stethoscope when the device is being used. This invention further incorporates a design structure that offers improved acoustic characteristics. Furthermore, the disclosed invention may be used as a stethoscope head cover together in conjunction with the rigid diaphragm that comes standard on the stethoscope head.

2. Description of the Related Art

The prior art in the field discloses several solutions to controlling the spread of diseases by a stethoscope. However, the prior art have failed to disclose a easy to apply sterile device that achieves minimal sound distortion and remains sterile throughout its use by incorporating anti-microbial agents.

U.S. Pat. No. 6,019,187 issued on Feb. 1, 2000 discloses a stethoscope cover that can be used without the supplied diaphragm in the stethoscope. However, this invention discloses a device that is comprised of rigid materials, and is therefore less conducive to carrying or transmitting sound vibrations. Additionally, this invention does not disclose a device impregnated with anti-microbial agents helping eliminate the spread of bacteria and other pathogens to the stethoscope cover as well as to other patients, but only acts as a protective barrier between the stethoscope head and a patient's skin.

U.S. Pat. No. 5,949,032 issued on Sep. 7, 1999 discloses a disposable stethoscope cover used to prevent transferring bacteria from one patient to another patient. This device, however, requires the application of an adhesive for the cover to be supplied to the stethoscope. The application of an adhesive makes this device difficult to use and also has a tendency to diminish the quality of sound reproduction as the adhesives build up between the cover and the stethoscope head.

U.S. Pat. No. 5,747,751 issued on May 5, 1998 and U.S. Pat. No. 5,428,193 issued on Jun. 27, 1995 disclose a flexible disposable cover for a stethoscope head. But this invention fails to neither disclose a device that is manufactured having sterile properties nor have any agents that act to kill harmful bacteria when they come in contact with the cover. Furthermore, this device can only be used in conjunction with the diaphragm that is supplied with the stethoscope and does not itself act as the stethoscope diaphragm itself.

This invention significantly improves on the teachings of the prior art by teaching a device that is elastomeric in design offering ease of use, improved sound conduction and inexpensive. Specifically this disclosed invention teaches a disposable stethoscope diaphragm or stethoscope cover offering anti-microbial properties resulting from the implantation of certain anti-microbial agents when the device is manufactured.

SUMMARY OF THE INVENTION

It is an object of this invention to provide a disposable stethoscope diaphragm that is inexpensive and which replaces the rigid diaphragm that is supplied with an original stethoscope.

It is another object of this invention to provide a disposable stethoscope cover that is comprised of an elastomeric material which offers sufficient flexibility, is nonporous, and is resistant to fluid penetration.

It is another object of this invention to provide a disposable elastomeric stethoscope diaphragm that is sterile when manufactured and is impregnated with anti-microbial agents, such as, but not limited to, silver, which serves to ensure that sterility is maintained and to prevent the spread of harmful bacteria to the disposable diaphragm in addition to protecting the stethoscope head from contamination.

It is another object of this invention to provide a disposable elastomeric stethoscope diaphragm that prevents transmission of harmful bacteria and other pathogens from the skin of the patient to the stethoscope head.

It is another object of this invention to provide a disposable elastomeric stethoscope diaphragm that prevents viruses and other pathogens from being transferred to the patient's skin from the stethoscope head.

It is another object of this invention to provide a disposable elastomeric stethoscope diaphragm that both improves sound amplification and minimizes distortion when placed over the head of the stethoscope.

It is another object of this invention to provide a disposable elastomeric stethoscope diaphragm being formed and specifically sized as to have an airtight seal with the stethoscope head when the invention is secured which thereby reduces sound distortion and improves the amplitude of the sound transmission through the disclosed device.

It is another object of this invention to provide a disposable elastomeric stethoscope diaphragm that can be easily placed over the stethoscope head and easily removed to be discarded.

It is another object of this invention to provide a disposable elastomeric stethoscope diaphragm that does not require adhesive to be applied to the stethoscope head.

It is another object of this invention to provide a disposable elastomeric stethoscope diaphragm cover that does not require a dispensing unit.

It is another object of this invention to provide a disposable elastomeric stethoscope diaphragm that does not create a vacuum with a patient's skin after the stethoscope is pressed against the patient's skin.

It is another object of this invention to provide a disposable elastomeric stethoscope diaphragm cover that can be used in conjunction with the rigid diaphragm that comes with a stethoscope and act solely as a cover for the stethoscope head with the rigid diaphragm still in place.

It is another object of this invention to provide a disposable elastomeric stethoscope diaphragm cover that is manufactured with sterile material and is further impregnated with anti-microbial agents.

It is another object of this invention to provide a disposable elastomeric stethoscope diaphragm cover being shaped and specifically sized resulting in improved sound conduction properties such that the device does not diminish sound quality by creating an airtight seal with the stethoscope head which minimizes distortion and maximizes sound amplitude.

It is another object of this invention to provide an elastomeric disposable stethoscope diaphragm cover that is easily secured to the stethoscope head and easily removed in order that the device may be discarded.

BRIEF DESCRIPTION OF THE DRAWINGS

FIG. 1 depicts a cross-section of a disposable diaphragm for a stethoscope according to an embodiment of the present invention.

FIG. 2 depicts the disposable stethoscope diaphragm being placed over a stethoscope head according to another embodiment of the present invention.

FIG. 3 depicts the disposable stethoscope diaphragm having been placed over the stethoscope head according to another embodiment of the present invention.

FIG. 4 depicts a schematic side view of a secured disposable diaphragm that is secured to a stethoscope head without the rigid diaphragm according to another embodiment of the present invention.

FIG. 5 depicts a schematic side view of a secured disposable diaphragm cover that is secured to a stethoscope head with the rigid diaphragm in place according to another embodiment of the present invention.

FIG. 6 depicts a schematic side view a secured disposable diaphragm having the raised contact surface being applied to skin.

DETAILED DESCRIPTION OF THE INVENTION

FIG. 1 depicts an embodiment of the invention known as a removable elastomeric diaphragm 101 that is used to address the problem of diseases and viruses being spread from one patient to another patient. The device is comprised of a molded elastomeric material forming a round piece of elastomer, forming the base portion, and further having a curved peripheral edge 102 which is molded to create opening 103. The diameter of opening 103 in its relaxed stated, or unstretched, is smaller than the diameter of the base portion 104 of the disclosed elastomeric diaphragm 101.

FIG. 2 displays the embodiment of the elastomeric diaphragm 101 being placed over the head of a stethoscope 105. The disclosure depicts the elastomeric diaphragm 101 being comprised of a sufficiently flexible material such that when applied to the stethoscope head 105, the elastomeric diaphragm 101 easily stretches around stethoscope head 105 and returning to its original shape. Furthermore, FIG. 2 depicts the elastomeric diaphragm having opening 103 with a diameter smaller than the diameter of the stethoscope head 105, such that the elastomeric diaphragm needs to be stretched in order to enlarge the opening 103 to fit around stethoscope head 105 which thereby creates an airtight seal between elastomeric diaphragm 101 and stethoscope head 105. Specifically, stethoscope head 105 is placed through opening 103 in the disclosed invention, a portion of the peripheral edge 102 is then secured over the outer rim of stethoscope head 105, and then the remainder of the peripheral edge 102 is stretched around the remainder of the outer rim of stethoscope head 105.

FIG. 3 depicts an embodiment of elastomeric diaphragm 101 in the final position after the device has been placed over the stethoscope head 105. The device is comprised of materials that are sufficiently elastic so that the device may be stretched open and then after tension is released the peripheral edge 102 of the elastomeric diaphragm 101 fits snugly against the exterior side of the rim of the stethoscope head 105 creating an airtight seal such that distortion is minimized and amplitude is maintained. The device is manufactured in different sizes so that a larger elastomeric diaphragm 101 and a smaller elastomeric diaphragm 106 may be attached to either the larger stethoscope head 105 (the diaphragm side) or the smaller stethoscope head 107 (the bell side of the stethoscope), as well as fitting various size larger heads and smaller sized stethoscope heads.

FIG. 4 depicts a side view schematic of elastomeric diaphragm 101, which has been fitted against a stethoscope head 105. The figure shows that the peripheral edge 102 of the elastomeric diaphragm 101 fits securely against the exterior of the rim extending from the housing of stethoscope head 105. FIG. 4 further shows a stethoscope head 105 with the rigid diaphragm 108 removed, and where the elastomeric diaphragm 101 is used instead as both the stethoscope's diaphragm transmitting sound energy and as a cover for the stethoscope to prevent the spread of infections and other bacteria between different patients.

FIG. 5 depicts a side view schematic drawing of elastomeric diaphragm 101 with peripheral edge 102 securely fit around the outside of the stethoscope head 105 housing. Furthermore in this depiction, the device is used as a cover for the stethoscope head 105 and the existing diaphragm 108 still in place, such that the elastomeric diaphragm 101 is used solely as a cover for stethoscope head 105 in order to prevent cross-contamination between different patients being examined with the same medical equipment.

FIG. 6 depicts a side view schematic drawing of elastomeric diaphragm 101 being securely fastened to stethoscope head 105 and being applied to patient's skin 110.

Specifically, FIG. 6 depicts raised portions 109 located at the outside center of the elastomeric diaphragm 101, such that the raised portions 109 allow elastomeric diaphragm 101 to be placed on patient's skin 110 and then subsequently removed without creating a vacuum between the elastomeric diaphragm 101 and patients skin 110. Whereas, if a vacuum is created by the application of the elastomeric diaphragm 101 to patient's skin 110 without raised portion 109, then a loud auditory pop is transmitted through the stethoscope to the user's ear thereby allowing potential damage to the ear when elastomeric diaphragm 101 is removed from patient's skin 110.

We claim:

1. An elastomeric disposable soft diaphragm adapted for a stethoscope head having a removable rigid diaphragm, said rigid diaphragm having been removed, and an exterior rim, wherein said disposable diaphragm replaces said removed rigid diaphragm and acts as a replacement diaphragm, wherein said disposable diaphragm comprises a central base portion having a first diameter and a curved peripheral edge, and wherein said first diameter is less than said diameter of said exterior rim of said stethoscope cavity, and wherein said curved peripheral edge forms an opening having a second diameter, wherein said second diameter is less than said first diameter, and wherein the elastomeric properties of said disposable diaphragm exhibit sufficient elasticity to allow said diaphragm to stretch to cover all commercially available stethoscope heads and then retract to the point whereby said curved peripheral edge of said soft diaphragm secures to and maintains an airtight seal with said exterior rim of said stethoscope head.

2. The device in claim 1 is manufactured sterile.

3. The device in claim 1 is manufactured using elastomer impregnated with an anti-microbial agent.

4. The device in claim 1 is sprayed with said anti-microbial agent after its manufacture is complete.

5. The device in claim 1 remains sterile between uses and does not require replacement each time after coming in contact with each human body.

6. The device in claim 1 has low thermal conductivity and feels warm when placed on the patient's skin.

7. The device in claim 1 has a durometer measurement in the Shore A classification.

8. The device in claim 1 is used as a replaceable, disposable cover for a rigid diaphragm, whereby said cover is stretched over the rigid diaphragm of the stethoscope, and whereby said cover stretches to cover all commercially available stethoscope rigid diaphragms and then retracts to the point whereby said curved peripheral edge secures to and maintains an airtight seal with said exterior rim of said stethoscope head.

9. The device in claim 8 is manufactured sterile.

10. The device in claim 8 is manufactured using elastomer impregnated with an anti-microbial agent.

11. The device in claim 8 is sprayed with said anti-microbial agent after its manufacture is complete.

12. The device in claim 8 remains sterile between uses and does not require replacement each time after coming in contact with each human body.

13. The device in claim 8 has low thermal conductivity and feels warm when placed on the patient's skin.

14. The device in claim 8 has a durometer measurement in the Shore A classification.

* * * * *